United States Patent [19]

Hoeffkes et al.

[11] Patent Number: 4,919,923
[45] Date of Patent: Apr. 24, 1990

[54] COSMETIC EMULSIONS HAVING IMPROVED FLOW BEHAVIOR

[75] Inventors: Horst Hoeffkes, Duesseldorf; Fritz Lange, Essen; Achim Ansmann, Hilden, all of Fed. Rep. of Germany

[73] Assignee: Henkel Kommanditgesellschaft auf Aktien, Duesseldorf, Fed. Rep. of Germany

[21] Appl. No.: 293,733

[22] Filed: Jan. 5, 1989

Related U.S. Application Data

[63] Continuation of Ser. No. 112,798, Oct. 23, 1987.

[30] Foreign Application Priority Data

Oct. 24, 1986 [DE] Fed. Rep. of Germany ....... 3636256

[51] Int. Cl.$^5$ .................... A61K 7/06; A61K 7/09; A61K 7/48
[52] U.S. Cl. ...................... 424/70; 514/772; 514/938
[58] Field of Search ............. 424/70; 514/772, 846, 514/938, 943

[56] References Cited

U.S. PATENT DOCUMENTS 4,009,254 2/1977 Renold .................. 424/59

FOREIGN PATENT DOCUMENTS 0058853 2/1982 European Pat. Off. .
0837997 7/1949 Fed. Rep. of Germany .
7305941 6/1971 Japan .
7333037 8/1971 Japan .

OTHER PUBLICATIONS

Chemical Abstracts 79:57575b.
Chemical Abstracts 79:96851h.

Primary Examiner—Ellis P. Robinson
Assistant Examiner—Susan S. Rucker
Attorney, Agent, or Firm—Ernie G. Szoke; Wayne C. Jaeschke; Norvell E. Wisdom

[57] ABSTRACT

Cosmetic emulsions of the oil-in-water type which are pourable at 20° C. contain as an oil component dialkyl ethers corresponding to the formula $R^1$—O—$R^2$, in which $R^1$ and $R^2$ independently of one another represent a linear or single-branch $C_{6-22}$ alkyl. Even a content of only 0.5 to 5% by weight of dialkyl ethers can considerably reduce the viscosity of the emulsions. Preferred emulsions contain from 1 to 30% by weight of discontinuous lipophilic phase and from 70 to 99% by weight of continuous aqueous phase.

18 Claims, No Drawings

COSMETIC EMULSIONS HAVING IMPROVED FLOW BEHAVIOR

This application is a continuation of application Ser. No. 07/112,798, filed 10/23/87.

BACKGROUND OF THE INVENTION

1. Field of the Invention

This invention relates to cosmetic emulsions of the oil-in-water (o/w) type which are pourable at ambient temperatures and which show high-stability and improved flow behavior.

2. Statement of Related Art

The viscosity and rheological behavior of oil-in-water emulsions have a major bearing on their stability and performance properties. For example, it is known that the stability of emulsions increases with increasing viscosity. Accordingly, cosmetic creams often contain consistency-generating (thickening) components, such as fatty alcohols, fatty acid partial glycerides or waxes which contribute significantly to the stability of the emulsion. However, there are many emulsions in which a liquid or pourable consistency is required for reasons of practical application. A reduction in viscosity can be achieved by reduction of the inner phase or by replacement of the consistency-generating components by more liquid components. However, any reduction of the inner phase is generally undesirable in terms of practical application because it impairs the strength and the appearance of the emulsion, i.e. the emulsions become transparent and visually unattractive in appearance. Omission or reduction of the consistency-generating components is often accompanied by a loss of emulsion stability.

Emulsions containing cationic emulsifiers, in which fatty alcohols and fatty acid partial glycerides are present as consistency-generating components and which are commonly used as liquid hair aftertreatment preparations, have the problem that fatty alcohols make hardly any contribution towards a creamy, rich appearance of the emulsions and that fatty acid partial glycerides actually reduce the conditioning effect. In addition, emulsions of the type in question show a tendency toward rethickening, i.e. they are in danger of undergoing a considerable increase in consistency or of completely losing their pourability after prolonged storage.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that pourable o/w emulsions having reduced viscosity and high stability in storage can be obtained providing $C_{6-22}$ dialkyl ethers are used as the oil component. Accordingly, the present invention relates to cosmetic o/w emulsions which are pourable at ambient temperatures, especially 19°–22° C., and which contain as oil components at least one dialkyl ether corresponding to the formula $R^1$—O—$R^2$, in which each of $R^1$ and $R^2$, independently of one another, are a linear or single-branch $C_{6-22}$ alkyl.

Some dialkyl ethers corresponding to the formula $R^1$—O—$R^2$ are known from the literature. Those dialkyl ethers which are not already known from the literature may readily be obtained by generally known methods, for example from alcohols by elimination of water or by alkylation of alcohols with alkyl halides or alkyl sulfates. The production of symmetrical dialkyl ethers is described, inter alia, by R. Perron and Ch. Paquot in Compt. rend. 231, 237–238 (1950). The production of asymmetrical dialkyl ethers by alkylation of alcohols with alkyl sulfuric acid monoester salts is described below in detail.

Mixtures of the inventive dialkyl ethers and standard cosmetic oil and fat components may also be used as the oil components for the production of o/w emulsions according to the invention. Surprisingly, a content of only 0.5 to 5% by weight preferably 0.5 to 3.0%, more preferably 0.5 to 2.0% of the inventive dialkyl ethers in addition to standard oil and fat components, based on the emulsion as a whole, is capable of significantly reducing the viscosity of the emulsion. Accordingly, it is also immaterial if the dialkyl ethers are not used in pure form, but may be employed in the form of a mixture with the starting alcohols used for their production.

The viscosity-reducing effect of the dialkyl ethers is generally discernible in o/w emulsions, although it is of particular practical value in emulsions of the type which are intended to be pourable at 20° C. The emulsions in question are preferably o/w emulsions containing from 70 to 99% (more preferably 75 to 95%) by weight of continuous (outer) aqueous phase, with the balance q.s. to 100% of discontinuous (inner) lipophilic phase.

The lipophilic phase consists essentially of standard cosmetic or pharmaceutical oil components, fats and/or waxes, oil-soluble emulsifiers and, optionally, oil soluble pharmaceutical or cosmetic active principles. In addition to the dialkyl ethers present in accordance with the invention, the cosmetic oil components present may be any of the vegetable, animal, mineral and synthetic oils known for this purpose, such as olive oil, sunflower oil, corn oil, mink oil, paraffin oil, silicone oils (for example dimethylpolysiloxane), squalene, oleyl alcohol, 2-octyldodecanol, decyloleate, isopropylmyristate, isononylstearate, 2-ethylhexyl palmitate, glycerol tricaprylate and other esters, alcohols or hydrocarbons known as cosmetic oil components. Suitable cosmetic fats and waxes are any of the products known for this purpose having melting points of up to about 80° C., such as hardened vegetable and animal fats (triglycerides), fatty alcohols, for example cetyl alcohol, stearyl alcohol, esters, such as cetyl palmitate, and natural waxes, such as wool wax, beeswax, japan wax, carnauba wax, candelilla wax, mineral waxes such as montan wax, paraffins, vaseline, and synthetic paraffins such as polyethylene waxes.

Suitable oil-soluble emulsifiers are any oil-soluble emulsifers suitable for the emulsification of the above-mentioned oils, fats and waxes. Examples include the soaps of $C_{12-22}$ fatty acids, the mono- and diglycerides and the sorbitan partial esters of $C_{12-22}$ fatty acids and the adducts of from 2 to 30 mols ethylene oxide with such fatty acid partial glycerides and sorbitan fatty acid esters, the adducts of from 2 to 30 mols ethylene oxide with $C_{12-22}$ fatty alcohols, with $C_{12-22}$ fatty acids, with $C_{8-16}$ alkylphenols and fatty acid alkanolamides, $C_{16-22}$ fatty alcohol sulfates in the form of their alkali or alkanolammonium salts, the phosphoric acid esters of linear fatty alcohols or of fatty alcohol polyglycol ethers in the form of the alkali or alkanolammonium salts.

One preferred embodiment of the invention are o/w emulsions which contain at least one surface active quaternary ammonium salt as an emulsifier. Particularly suitable quaternary ammonium salts are those corresponding to the formula

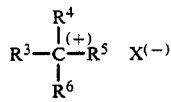

wherein: $R^3$ is a $C_{12-22}$ alkyl; $R^4$ is a $C_{1-4}$ alkyl, benzyl, or $R^3$; $R^5$ and $R^6$ are each a $C_{1-4}$ alkyl or $C_{2-4}$ hydroxyalkyl; and $X^{(-)}$ is chloride, bromide, or $R^7-O-SO_3^{(-)}$, where $R^7$ is a $C_{1-4}$ alkyl. These cationic emulsifiers, often in the form of aqueous solutions, are used in an emulsifier-effective amount, preferably in a quantity of from 0.2 to 2%, more preferably 0.2 to 1.0%, most preferably 0.3 to 0.7% as active salt by weight of the total emulsion.

Examples of preferred quaternary ammonium salts are cetyltrimethylammonium chloride, stearyltrimethylammonium chloride and distearyldimethylammonium chloride.

In addition to the constituents mentioned above, the discontinuous lipophilic phase may also contain oil soluble active substances, such as light stabilizers, antioxidants, vitamins, oil soluble preservatives (for example p-hydroxybenzoic acid benzyl ester), or pharmaceutical active principles.

In addition to water, the continuous aqueous phase may contain other water soluble auxiliaries, for example: polyols such as glycerol or sorbitol; water soluble salts such as magnesium sulfate; buffer substances such as alkali phosphate, alkali citrate, or borates; water soluble preservatives such as p-hydroxybenzoic acid methyl ester or sorbic acid; water soluble polymers such as carboxy methyl celluloses or carboxyvinyl polymers; water soluble surface active substances or emulsifiers; water soluble dyes; or water soluble cosmetic or pharmaceutical active principles such as vegetable extracts, proteins or protein derivatives, amino acids, etc.

The o/w emulsions according to the invention are distinguished by reduced viscosity, but nevertheless show high stability and an attractive, creamy appearance so that the emulsions are not transparent, even when applied in thin layers. The tendency towards rethickening, i.e. towards an increase in viscosity in the event of prolonged storage, is distinctly reduced. A good hair-conditioning effect is obtained with cationic o/w emulsions according to the invention when used as hair aftertreatment preparations. Moreover, cationic emulsions of this type also give the skin a desireable soft, velvety feel. The following Examples illustrate the invention without limiting it.

EXAMPLES

1. Preparation of n-octyl-cetyl/stearyl ether 2604 g (20 mol) n-octanol-1 and 360.6 g of a 30% by weight solution of sodium methylate in methanol were combined and the methanol distilled off by heating to 150° C. (in a nitrogen atmosphere). 686 g (2 mols) of cetyl-/stearyl (1:1) sulfate sodium salt (powder, 90%) were then added in portions, after which the reaction mixture was heated to 175° C. and stirred for 8 hours at that temperature. After cooling to 90° C., the reaction mixture was mixed with 1 liter of water. The organic phase was separated off and washed twice with water. 758 g of a colorless solid having a residual hydroxyl number of 29.1 were obtained.

2. Preparation of n-octadecyl-cetyl/stearyl ether 39 kg of n-octadecanol (144 mols) and 8.6 kg of 30% sodium methylate solution were initially introduced under nitrogen into a reactor and heated to 150° C., methanol distilling off. After 1 hour, 10.4 kg of cetyl-/stearyl (1:1) sulfate sodium salt (powder, 90%) were added at that temperature, followed by stirring for 1 h at 175° C. The ether formed served as additional solvent. Another 10.4 kg cetyl-/stearyl (1:1) sulfate were added, followed by stirring for 8 hours at 175° C. After cooling to 100° C., 40 kg of n-hexanol were added. After washing twice with water, the product was freed from n-hexanol and excess n-octadecanol by distillation. 23.4 kg of a wax-like product having a residual hydroxyl number of 31 were obtained.

3. Hair Rinses were prepared by mixing

TABLE 1

| Ingredient/Property | Example 1.1 (comparison) | Example 1.2 (invention) | Example 1.3 (comparison) |
|---|---|---|---|
| Di-n-dodecyl ether | — | 1.5 | — |
| Cetyl/stearyl alcohol | 3 | 1.5 | 1.5 |
| Glycerol mono/dipalmitate/stearate | — | — | 1.5 |
| Cetyltrimethylammonium chloride (30% solution) | 2.0 | 2.0 | 2.0 |
| Water | 95 | 95 | 95 |
| Appearance | opaque transparent | white creamy | white creamy |
| Viscosity mPa.s (cps), 20° C. Brookfield RVT, spindle 4, 20 r.p.m. | | | |
| after 24 hours | 1525 | 725 | 1650 |
| after 30 days | 2800 | 750 | 2500 |
| Conditioning effect | very good | very good | good |

It should be noted that Comparison Examples 1.1 and 1.3 had undesireably high initial viscosities, which increased even more, to completely unacceptable levels. Moreover, Example 1.1 has a very undesireable appearance and Example 1.3 a lower conditioning effect. By contrast, Invention Example 1.2 had an excellent appearance, a desireably low initial viscosity, evidenced viscosity stability upon storage, and had a very good conditioning effect.

4. Skin care lotions were prepared by mixing

TABLE 2

| Ingredient/Property | Example 2.1 comparison | Example 2.2 invention | Example 2.3 invention |
|---|---|---|---|
| Di-n-dodecyl ether | — | 0.5 | 1.0 |
| n-octyl-cetyl/stearyl ether | — | — | — |
| Paraffin oil (perliquidum) | 4.0 | 4.0 | 4.0 |
| Isopropyl palmitate | 8.0 | 8.0 | 8.0 |
| Silicone oil (M 300) | — | — | — |
| Cetyl/stearyl alcohol | 1.0 | 0.5 | — |
| Cetyl/stearyl alcohol poly-(12)-glycol ether | 1.5 | 1.5 | 1.5 |
| Stearic acid | 1.0 | 1.0 | 1.0 |
| Triethanolamine | 0.6 | 0.6 | 0.6 |
| p-hydroxybenzoic acid methyl ester | 0.1 | 0.1 | 0.1 |
| p-hydroxybenzoic acid propyl ester | 0.1 | 0.1 | 0.1 |

TABLE 2-continued

| Ingredient/Property | Example 2.1 comparison | 2.2 invention | 2.3 invention |
|---|---|---|---|
| Polyacrylic acid anionic emulsifier/thickener (Carbopol"940, a trademark of B.F. Goodrich Chemical) | 0.2 | 0.2 | 0.2 |
| Glycerol | 4.0 | 4.0 | 4.0 |
| Perfume oil | — | — | — |
| Water | 79.5 | 79.5 | 79.5 |
| Appearance | white, dim | white, shiny | white, shiny |
| Viscosity mPa.s (cps), 20° C. Brookfield RVT, spindle 5, 10 r.p.m. | | | |
| after 1 hour | 29,200 | 17,200 | 15,400 |
| after 24 hours | 32,800 | 23,600 | 17,000 |

5. Cationic skin care lotions

TABLE 3

| Ingredient/Property | Example 2.4 comparison | 2.5 invention |
|---|---|---|
| Di-n-dodecyl ether | — | — |
| n-octyl-cetyl/stearyl ether | — | 2.0 |
| Paraffin oil (perliquidum) | 5.0 | 5.0 |
| Isopropyl palmitate | 3.0 | 3.0 |
| Silicone oil (M 300) | 1.0 | 1.0 |
| Cetyl/stearyl alcohol | 1.5 | — |
| Cetyl/stearyl alcohol poly-(12)-glycol ether | 0.3 | 0.3 |
| Distearyldimethylammonium chloride (70% solution) | 0.5 | 0.5 |
| Stearic acid | — | — |
| Triethanolamine | — | — |
| p-hydroxybenzoic acid methyl ester | 0.2 | 0.2 |
| p-hydroxybenzoic acid propyl ester | 0.1 | 0.1 |
| Polyacrylic acid anionic emulsifier/thickener (Carbopol"940, a trademark of B.F. Goodrich Chemical) | — | — |
| Glycerol | 3.0 | 3.0 |
| Perfume oil | 0.3 | 0.3 |
| Water | 85.1 | 84.6 |
| Appearance | white, weak, translucent | white, bright, creamy |

It should be noted that Comparison Example 2.1 had an unacceptably high initial viscosity, which increased upon storage. By contrast, Inventive Examples 2.2 and 2.3 had considerably lower initial viscosities which, even after 24 hours, did not reach that of Comparison Example 2.1.

The inventive examples 2.2, 2.3 and 2.5 had a bright and shiny or creamy appearance while the comparative examples 2.1 and 2.4 looked dim, weak and translucent.

We claim:

1. An oil in water cosmetic emulsion comprising about 70 to about 99% by weight of aqueous phase and between about 0.5 and about 5.0% by weight, based on the total composition, of at least one dialkyl ether of the formula $R^1—O—R^2$, wherein $R^1$ and $R^2$ each are, independently, a linear or single-branch $C_{6\text{-}22}$ alkyl.

2. The emulsion of claim 1 wherein said dialkyl ether is present in admixture with standard cosmetic oil, fat, and wax components having a melting point up to 80° C.

3. The emulsion of claim 1 wherein a surface-active quaternary ammonium salt or aqueous solution thereof is present in an emulsifier effective amount.

4. The emulsion of claim 2 wherein a surface-active quaternary ammonium salt or aqueous solution thereof is present in an emulsifier effective amount.

5. The emulsion of claim 1 wherein a surface-active quaternary ammonium salt or aqueous solution thereof is present in an emulsifier effective amount.

6. The emulsion of claim 2 wherein a surface-active quaternary ammonium salt or aqueous solution thereof is present in an emulsifier effective amount.

7. The emulsion of claim 3 wherein said quaternary ammonium salt has the formula

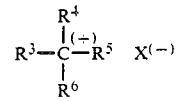

wherein:
$R^3$ is a $C_{12\text{-}22}$ alkyl;
$R^4$ is a $C_{1\text{-}4}$ alkyl, benzyl, or $R^3$;
$R^5$ and $R^6$ are each, independently, a $C_{1\text{-}4}$ alkyl or $C_{2\text{-}4}$ hydroxyalkyl; and
$X^{(-)}$ is chloride, bromide, or $R^7—O—SO_3^{(-)}$ where $R^7$ is a $C_{1\text{-}4}$ alkyl;
and is present in 0.2 to 2.0% by weight as active salt, based upon the weight of the total emulsion.

8. The emulsion of claim 4 wherein said quaternary ammonium salt has the formula

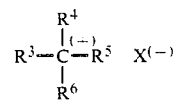

wherein:
$R^3$ is a $C_{12\text{-}22}$ alkyl;
$R^4$ is a $C_{1\text{-}4}$ alkyl, benzyl, or $R^3$;
$R^5$ and $R^6$ are each, independently, a $C_{1\text{-}4}$ alkyl or $C_{2\text{-}4}$ hydroxyalkyl; and
$X^{(-)}$ is chloride, bromide, or $R^7—O—SO_3^{(-)}$ where $R^7$ is a $C_{1\text{-}4}$ alkyl;
and is present in 0.2 to 2.0% by weight as active salt, based upon the weight of the total emulsion.

9. The emulsion of claim 5 wherein said quaternary ammonium salt has the formula

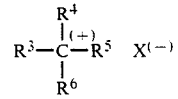

wherein:
$R^3$ is a $C_{12\text{-}22}$ alkyl;
$R^4$ is a $C_{1\text{-}4}$ alkyl, benzyl, or $R^3$;
$R^5$ and $R^6$ are each, independently, a $C_{1\text{-}4}$ alkyl or $C_{2\text{-}4}$ hydroxyalkyl; and
$X^{(-)}$ is chloride, bromide, or $R^7—O—SO_3^{(-)}$ where $R^7$ is a $C_{1\text{-}4}$ alkyl;
and is present in 0.2 to 2.0% by weight as active salt, based upon the weight of the total emulsion.

10. The emulsion of claim 6 wherein said quaternary ammonium salt has the formula

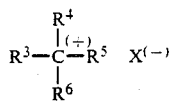

wherein:
- $R^3$ is a $C_{12-22}$ alkyl;
- $R^4$ is a $C_{1-4}$ alkyl, benzyl, or $R^3$;
- $R^5$ and $R^6$ are each, independently, a $C_{1-4}$ alkyl or $C_{2-4}$ hydroxyalkyl; and
- $X^{(-)}$ is chloride, bromide, or $R^7-O-SO_3^{(-)}$ where $R^7$ is a $C_{1-4}$ alkyl;

and is present in 0.2 to 2.0% by weight as active salt, based upon the weight of the total emulsion.

11. The emulsion of claim 1 wherein said dialkyl ether is an n-octyl-cetyl/stearyl ether, an n-octadecyl-cetyl/stearyl ether, or a mixture thereof.

12. The emulsion of claim 2 wherein said dialkyl ether is an n-octyl-cetyl/stearyl ether, an n-octadecyl-cetyl/stearyl ether, or a mixture thereof.

13. The emulsion of claim 3 wherein said dialkyl ether is an n-octyl-cetyl/stearyl ether, an n-octadecyl-cetyl/stearyl ether, or a mixture thereof.

14. The emulsion of claim 7 wherein said dialkyl ether is an n-octyl-cetyl/stearyl ether, an n-octadecyl-cetyl/stearyl ether, or a mixture thereof.

15. The emulsion of claim 10 wherein said dialkyl ether is an n-octyl-cetyl/stearyl ether, an n-octadecyl-cetyl/stearyl ether, or a mixture thereof.

16. The emulsion of claim 3 wherein said quaternary ammonium salt is cetyltrimethylammonium chloride, stearyltrimethylammonium chloride, distearyldimethylammonium chloride, or a mixture thereof.

17. The emulsion of claim 14 wherein said quaternary ammonium salt is cetyltrimethylammonium chloride, stearyltrimethylammonium chloride, distearyldimethylammonium chloride, or a mixture thereof.

18. The emulsion of claim 15 wherein said quaternary ammonium salt is cetyltrimethylammonium chloride, stearyltrimethylammonium chloride, distearyldimethylammonium chloride, or a mixture thereof.

* * * * *